United States Patent [19]

Smith et al.

[11] 4,431,644
[45] Feb. 14, 1984

[54] ANTIHYPERTENSIVE AGENTS

[75] Inventors: Elizabeth M. Smith, Verona; Joseph T. Witkowski, Morris Township, Morris County; Ronald J. Doll, Maplewood, all of N.J.

[73] Assignee: Schering Corporation, Kenilworth, N.J.

[21] Appl. No.: 355,638

[22] Filed: Mar. 8, 1982

[51] Int. Cl.³ .................. C07D 285/24; A61K 31/40; A61K 31/54; C07D 417/12
[52] U.S. Cl. .................................... 424/246; 424/274; 544/13; 548/452; 548/533
[58] Field of Search .................. 548/452, 533; 544/13; 424/246, 274

[56] References Cited

U.S. PATENT DOCUMENTS 3,110,716 11/1963 McLamore et al. .................. 544/13

FOREIGN PATENT DOCUMENTS 2073187 10/1981 United Kingdom .

OTHER PUBLICATIONS

Cutting's Handbook of Pharmacology, 6th Ed., Chapter 20, pp. 190-195. (1979).

Primary Examiner—John M. Ford
Attorney, Agent, or Firm—Anita W. Magatti; Bruce M. Eisen

[57] ABSTRACT

Compounds of the formula

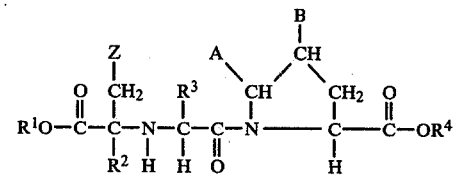

and the pharmaceutically acceptable salts thereof, wherein $R^1$, $R^2$ and $R^4$ are independently selected from hydrogen and lower alkyl; $R^3$ is hydrogen, lower alkyl or amino lower alkyl; A and B taken together with the carbons to which they are attached form an alkylene ring having six carbon atoms or A and B are hydrogen; and Z is

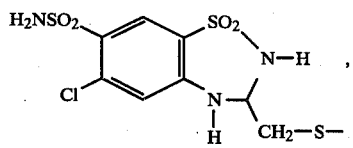

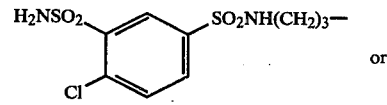

or

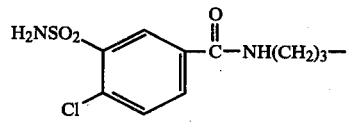

are disclosed. The compounds are useful as anti-hypertensive agents.

12 Claims, No Drawings

ANTIHYPERTENSIVE AGENTS

The present invention relates to carboxyalkyl dipeptides substituted with a benzothiadiazine, sulfamoylarenesulfonamido or sulfamoylarenecarboxamido group. The compounds are useful as antihypertensive agents.

The compounds of the present invention may be represented by the formula

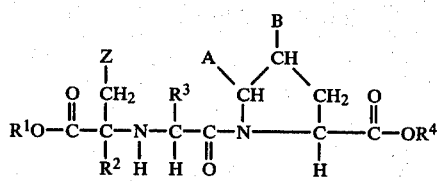

and the pharmaceutically acceptable salts thereof, wherein $R^1$, $R^2$ and $R^4$ are independently selected from hydrogen and lower alkyl; $R^3$ is hydrogen, lower alkyl or amino lower alkyl; A and B taken together with the carbons to which they are attached form an alkylene ring having six carbon atoms or A and B are hydrogen; and Z is

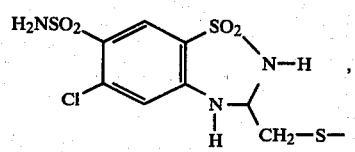

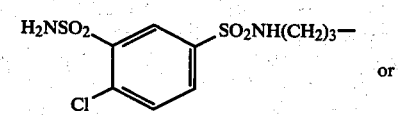

or

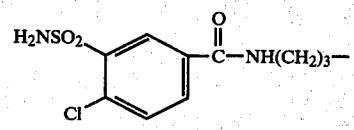

One aspect of the present invention relates to compounds of the formula

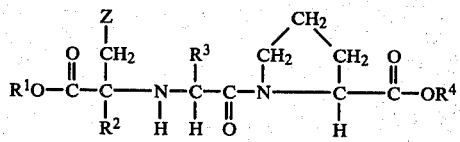

and the pharmaceutically acceptable salts thereof, wherein Z, $R^1$, $R^2$, $R^3$ and $R^4$ are as defined above.

Another aspect of the present invention relates to compounds of the formula

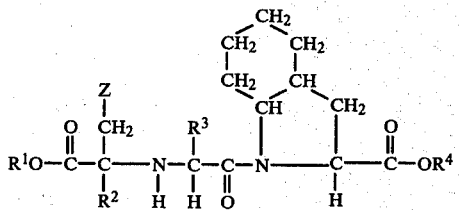

and the pharmaceutically acceptable salts thereof, wherein Z, $R^1$, $R^2$, $R^3$ and $R^4$ are as defined above.

One embodiment of the present invention relates to compounds of the formula

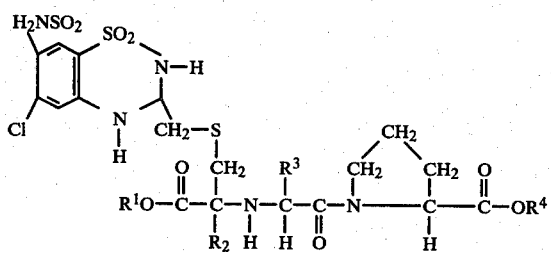

and the pharmaceutically acceptable salts thereof, wherein $R^1$, $R^2$, $R^3$ and $R^4$ are as defined above.

Another embodiment of the present invention relates to compounds of the formula

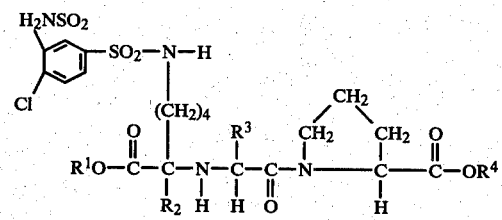

and the pharmaceutically acceptable salts thereof, wherein $R^1$, $R^2$, $R^3$ and $R^4$ are as defined above.

Another embodiment of the present invention relates to compounds of the formula

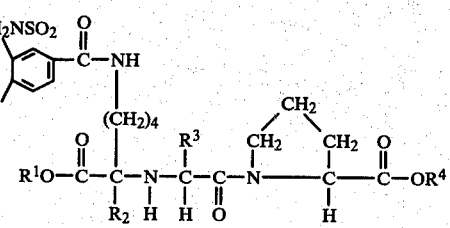

and the pharmaceutically acceptable salts thereof, wherein $R^1$, $R^2$, $R^3$ and $R^4$ are as defined above.

Another embodiment of the present invention relates to compounds of the formula

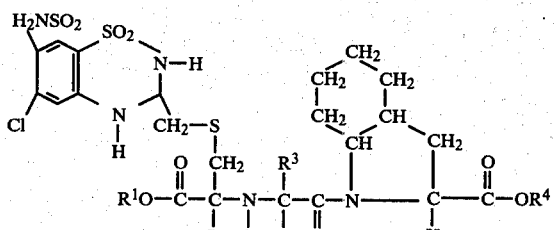

and the pharmaceutically acceptable salts thereof, wherein $R^1$, $R^2$, $R^3$ and $R^4$ are as defined above.

Another embodiment of the present invention relates to compounds of the formula

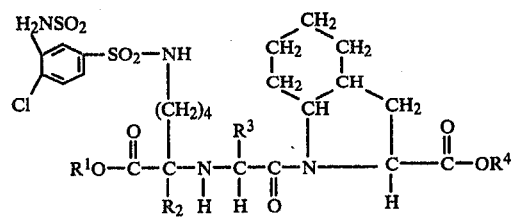

and the pharmaceutically acceptable salts thereof, wherein $R^1$, $R^2$, $R^3$ and $R^4$ are as defined above.

Another embodiment of the present invention relates to compounds of the formula

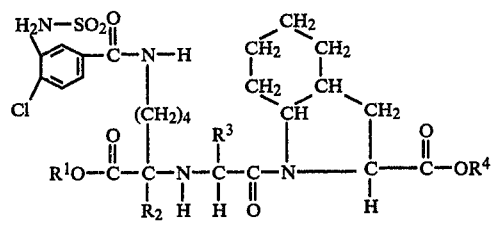

and the pharmaceutically acceptable salts thereof, wherein $R^1$, $R^2$, $R^3$ and $R^4$ are as defined above.

The aforementioned compounds of the formula I, as defined above, include various stereoisomers. Preferred stereoisomers are those in which the configurations adjacent to the nitrogen atoms correspond most closely to natural L-aminoacids. The lower alkyl groups, except where noted otherwise, include straight and branched chain hydrocarbon radicals from one to six carbon atoms, for example, methyl, ethyl, propyl, isopropyl, butyl, isobutyl, t-butyl, pentyl and the like.

Compounds of the present invention may be prepared as follows:

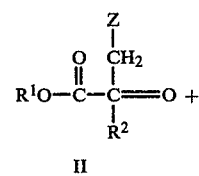

II

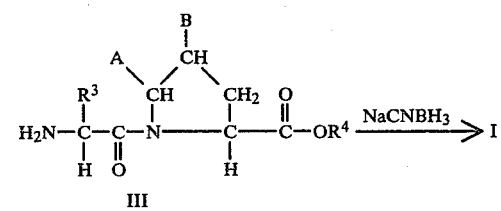

III

Keto acid (or ester) II is condensed with dipeptide III in aqueous solution, optimally near neutrality, or in a suitable organic solvent (for example, CH$_3$OH) in the presence of sodium cyanoborohydride to give I wherein $R^2$ is hydrogen. Alternatively, the intermediate Schiff base, enamine, or aminol may be catalytically reduced to yield product I wherein $R^2$ is hydrogen, for example, by hydrogen in the presence of 10% palladium on carbon or of Raney nickel. The ratio of diasteriomeric products formed may be altered by choice of catalyst.

If $R^1O$ is a carboxy protecting group such as alkoxy or benzyloxy, it can be converted by well known methods such as hydrolysis or hydrogenation to I, wherein $R^1O$ is hydroxy. This is also the case in all of the methods referred to below.

Alternatively, II can be condensed with amino acid IV under the same conditions to yield amino acid V

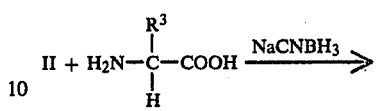

IV

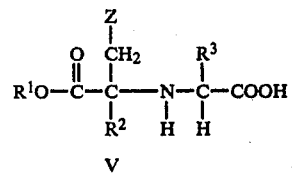

V

Subsequent coupling of V by known methods with amino acid derivative VI gives I

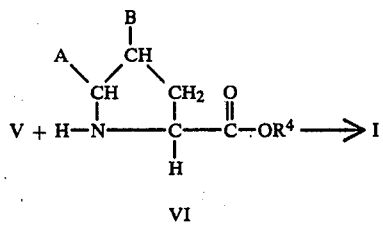

VI

Compounds of the present invention can also be obtained by reacting amino acid derivative VI with an α-keto acid chloride VII to give a substituted amino acid VIII

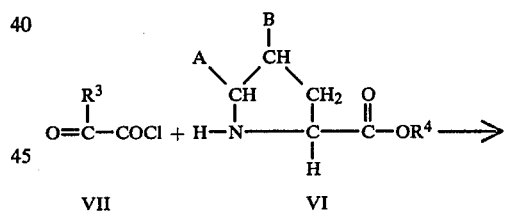

VII        VI

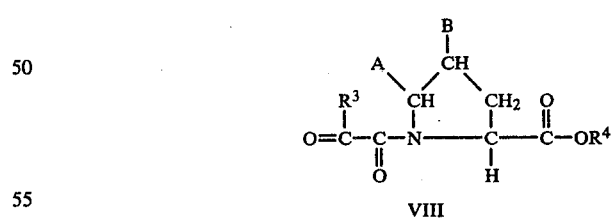

VIII

Subsequent condensation by known methods of amino acid IX with substituted amino acid VIII gives I

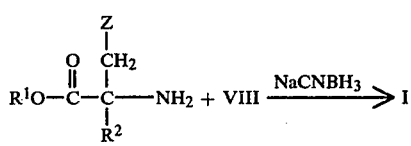

The known methods encompass reactive group protection during the coupling reaction, for example, by N-formyl, N-t-butoxycarbonyl and N-carbobenzyloxy groups followed by their removal to yield I. Furthermore, the carboxylic acid function in VI may be protected by removable ester groups such as benzyl, ethyl, t-butyl, and the like. Condensing agents in this synthetic route are typically those useful in peptide chemistry.

Compounds I, V or IX where Z is —(CH$_2$)$_3$NH$_2$ can be coupled with the appropriately substituted aroyl chloride or arenesulfonyl chloride in a suitable solvent (e.g. THF or pyridine) to form the respective amide or sulfonamide bond.

Compounds I, V, or IX where R$^1$ is —SCH$_2$Ph (wherein Ph represents phenyl) can be reduced with sodium in liquid ammonia followed by coupling with the appropriately substituted 3-halomethyl benzothiadiazine in a suitable solvent (e.g. DMF) to give I, V, or IX where Z is

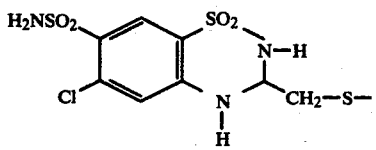

The compounds of the present invention include the following:

1-{N-[[1(R)-Carboxy-2-[S-((3-(6-chloro-3,4-dihydro-7-sulfamoyl-1,2,4-benzothiadiazinyl-1,1-dioxide)methyl))thio]ethyl]]-(S)-alanyl}-cis,syn-octahydro-1H-indole-2(S)-carboxylic acid;

1-{N-[[1(R)-Carboxy-2-[S-((3-(6-chloro-3,4-dihydro-7-sulfamoyl-1,2,4-benzothiadiazinyl-1,1-dioxide)methyl))thio]ethyl]]-(S)-alanyl}-(S)-proline;

1-{N-[[1(R)-Ethoxycarbonyl-2-[S-((3-(6-chloro-3,4-dihydro-7-sulfamoyl-1,2,4-benzothiadiazinyl-1,1-dioxide)methyl))thio]ethyl]]-(S)-alanyl}-cis,syn-octahydro-1H-indole-2(S)-carboxylic acid;

1-{N[[1(R)-Ethoxycarbonyl-2-[S-((3-(6-chloro-3,4-dihydro-7-sulfamoyl-1,2,4-benzothiadiazinyl-1,1-dioxide)methyl))-thio]ethyl]]-(S)-alanyl}-(S)-proline;

1-{N-[1(S)-Ethoxycarbonyl-5-(4-chloro-3-sulfamoyl)-benzenesulfonamidopentyl]-(S)-alanyl}-cis,syn-octahydro-1H-indole2(S)-carboxylic acid;

1-{N[1(S)-Ethoxycarbonyl-5-(4-chloro-3-sulfamoyl)-benzenesulfonamidopentyl]-(S)-alanyl}-(S)-proline;

1-{N-[1(S)-Ethoxycarbonyl-5-(4-chloro-3-sulfamoyl)-benzamidopentyl]-(S)-alanyl}-cis,syn-octahydro-1H-indole2(S)-carboxylic acid;

1-{N-[1(S)-Ethoxycarbonyl-5-(4-chloro-3-sulfamoyl)-benzamidopentyl]-(S)[alanyl]-(S)-proline;

1-{N-[1(S)-Carboxy-5-(4-chloro-3-sulfamoyl)benzamidopentyl]-(S)-alanyl}-cis,syn-octahydro-1H-indole-2(S)-carboxylic acid;

1-{N-[1(S)-Carboxy-5-(4-chloro-3-sulfamoyl)benzamidopentyl]-(S)-alanyl}-(S)-proline;

1-{N-[1(S)-Carboxy-5-(4-chloro-3-sulfamoyl)benzenesulfonamidopentyl]-(S)-alanyl}-cis,syn-octahydro-1H-indole-2(S)-carboxylic acid;

1-{N-[1(S)-Carboxy-5-(4-chloro-3-sulfamoyl)benzenesulfonamidopentyl]-(S)-alanyl}-(S)-proline.

EXAMPLE 1

1-{N-[1(R)-Ethoxycarbonyl-2-(benzylthio)ethyl]-(S)-alanyl}-cis,syn-octahydro-1H-indole-2(S)-carboxylic acid, hydrobromide A. Stir 100 g of S-benzyl-L-cysteine ethyl ester hydrochloride, 132 g of benzyl pyruvate, and 10 g of 3A molecular sieves in 8 liters of ethanol for 18 hours under nitrogen. Add dropwise a solution of 52 g of sodium cyanoborohydride in 100 ml of ethanol, stir at room temperature for 24 hours, filter, then concentrate the filtrate at room temperature under vacuum. Suspend the resultant residue in 100 ml of water and 500 ml of ether and adjust the mixture to pH 8 with 1 N HCl. Wash the organic layer with saturated sodium chloride solution, dry over sodium sulfate, and filter. Adjust the filtrate to pH 2 with 3 M ethereal HCl, decant the supernatant, wash the resulting oily precipitate with 200 ml of ether, and mix with saturated aqueous sodium bicarbonate to obtain a solution of pH 8. Extract the mixture with 1 liter of ether, dry the ether layer over sodium sulfate and concentrate at room temperature to give N-[1(R)-carboethoxy-2-(benzylthio)ethyl]-(R,S)-alanine, benzyl ester, an amber oil. Thin layer chromatography in ethyl acetate:hexane (15:85) may be used to separate the two isomers (isomer A at Rf=0.36, and isomer B at Rf=0.28), or the procedure may be continued on the mixture.

B. Add 50 g of the product of part A to 1800 ml of a 15-20% solution of hydrobromic-acetic acid and heat at 50° C. for 20 hours. Concentrate the resultant mixture to dryness under vacuum, and wash the resultant oily residue with ether until free of acetic acid to produce N-[1(R)-carboxyethyl-2(benzylthio)ethyl]-(R,S)-alanine hydrobromide, an amber oil.

C. Cool a solution of 50.5 g of the product of part B and 33.4 g of cis,syn-octahydroindole-2(S)-carboxylic acid benzyl ester in 1 liter of dimethylformamide to 0° C. under nitrogen, add dropwise a solution of 33.5 g of diphenylphosphorylazide in 1 liter of dimethylformamide, followed by a solution of 33.4 g of N-methylmorpholine in 200 ml of dimethylformamide, also added dropwise, and stir at room temperature for 18 hours. Pour the reaction solution into 3 liters of water, adjust to pH 8 with 1 N NaOH, and extract with 4×1 liter of ether. Wash the combined ether layers with 1 liter of aqueous sodium chloride, dry the ether layer over magnesium sulfate, filter, and concentrate under vacuum to an amber oil.

Chromatograph the resultant oil on 2 kg of silica gel (60–200 mesh) using ether:hexane (90:10). Collect components having Rf 0.38 and Rf 0.61 as indicated by thin layer chromatograhy on silica gel eluted with ether. The isomer with Rf 0.61 is 1-{N-[[1(R)-carboethoxy-2-(benzylthio)-ethyl]-(S)-alanyl}-cis,syn-octahydro-1H-indole-2(S)-carboxylic acid, benzyl ester.

D. Stir 0.70 g of the (S)-alanyl product of part C and 25 ml of a 15-20% solution of hydrobromic-acetic acid under nitrogen for 2 hours, then concentrate to dryness under vacuum at room temperature. Triturate the resultant residue with ether and filter to obtain 1-{N-[1(R)-carboethoxy-2-(benzylthio)-ethyl]-(S)-alanyl}-cis,syn-octahydro-1H-indole-2(S)-carboxylic acid, hydrobromide, as a tan solid, m.p. 124°–125° C.

EXAMPLE 2

1-{N-[1(R)-Carboxy-2-(benzylthio)ethyl]-(S)-alanyl}-cis,syn-octahydro-1H-indole-2(S)-carboxylic acid To a solution of 10.6 g of 1-{N-[1(R)-ethoxycarbonyl-2-(benzylthio)ethyl]-(S)-alanyl}cis,syn-octahydro-1H-indole-2(S)-carboxylic acid, hydrobromide in 500 ml of methanol, add 24 ml for 2.5 N sodium hydroxide solution and stir at room temperature for 24 hours. Concentrate this solution in vacuo and absorb on AG 50W-2 (Bio-Rad) resin (100–200 mesh, hydrogen form). Elute the resin with water and then elute with 4% pyridine in water to yield the title compound.

EXAMPLE 3

1-{N-[1(R)-Carboxy-2-(mercapto)ethyl]-(S)-alanyl}-cis,syn-octahydro-1H-indole-2(S)-carboxylic acid Treat 4.22 g of 1-{N-[1(R)-Carboxy-2-(benzylthio)ethyl]-(S)-alanyl}-cis,syn-octahydro-1H-indole-2(S)-carboxylic acid with 0.23 g of sodium in 200 ml of liquid ammonia. Evaporate the ammonia and absorb the residue on AG 50W-2 (Bio-Rad) resin (100–200 mesh, hydrogen form). Elute the resin with water and then elute with 4% pyridine in water to yield the title compound.

EXAMPLE 4

1-{N-[1(R)-Carboxy-2-[S-((3-(6-chloro-3,4-dihydro-7-sulfamoyl-1,2,4-benzothiadiazinyl-1,1-dioxide)methyl))-thio]ethyl]]-(S)-alanyl}-cis,syn-octahydro-1H-indole-2(S)-carboxylic acid React 2.2 g of 1- N-[1(R)-carboxy-2-(mercapto)ethyl](S)-alanyl-cis,syn-octahydro-1H-indole-2(S)-carboxylic acid in 20 ml of diemthylformamide with 2.4 g of 3-bromomethyl-6-chloro-3,4-dihydro-7-sulfamoyl-1,2,4-benzothiadiazine-1,1-dioxide and triethylamine. Concentrate the resulting mixture to give the title compound.

EXAMPLE 5A cis,syn-Octahydroindole-2(S)-carboxylic acid, benzyl ester

A. Dissolve 27.0 g of ethyl indole-2-carboxylate in 250 ml of trifluoroacetic acid. Add 2.05 g of platinium oxide, hydrogenate the mixture at 50 lb/in$^2$ at room temperature. Filter the mixture and concentrate the filtrate in vacuo to give a residue. Suspend the residue in ether and treat with cold dilute sodium hydroxide solution. Dry the organic layer over magnesium sulfate and concentrate it to give ethyl octahydroindole-2-carboxylate, a pale yellow oil.

B. Dissolve 116 g of 10-d-camphorsulfonic acid in 1 liter of warm ethyl acetate and add a solution of 86 g of the product of part A in 1 liter of ethyl acetate. Allow the mixture to crystallize, heat to reflux, cool to room temperature, and filter. Recrystallize the filter cake from a mixture of 500 ml of isopropanol and 1800 ml ethyl acetate, filter and dry the crystals to obtain 2-(S)-carboethoxy-cis,syn-octahydro-1H-indole, d-10-camphorsulfonate, m.p. 192°–193° C.

C. Slurry 10 g of the product of part B in 1 liter of ether, adjust to pH 11 with aqueous sodium hydroxide, and stir for 5 minutes. Wash the organic layer with sodium chloride solution, dry over magnesium sulfate, filter, and evaporate in vacuo at room temperature to obtain 2(S)-carboethoxy-cis,syn-octahydro-1H-indole as a colorless oil. Dissolve the resultant oil in 50 ml of methanol containing 23 ml of 1 N sodium hydroxide, stir at 25° C. for 30 minutes, adjust to pH 7 with 1 N hydrochloric acid, and evaporate the solvent to give cis,syn-octahydro-1H-indole-2(S)-carboxylic acid.

D. Cool 23 ml of benzyl alcohol to 0° C. under nitrogen and add 5.95 g of thionyl chloride dropwise over 15 minutes, maintaining the temperature at 0° C. Add the product of part C, stir for 1 hour at 0° C., then stir for 24 hours at room temperature. Pour the resulting mixture into 500 ml of ether, stir 1 hour under nitrogen, then allow to stand under nitrogen until the solution is clear. Decant the supernatant, wash the precipitate with 25 ml ether, then slurry the precipitate in 200 ml ether and adjust to pH 8–9 with 1 N sodium hydroxide. Stir 5 minutes, wash the organic layer with sodium, chloride solution, dry over magnesium sulfate, filter and evaporate in vacuo at room temperature to obtain the title compound as a colorless oil (TLC in ether: one spot, Rf 0.3).

EXAMPLE 5B

1-{N-[1(S)-Ethoxycarbonyl-5-aminopentyl]-(S)-alanyl}-cis,syn-octahydro-1H-indole-2(S)-carboxylic acid A. To 26 g of cis,syn-octahydro-1H-indole-2(S)-carboxylic acid, benzyl ester (prepared in Example 5A) in 100 ml of dichloromethane and 7.8 ml of pyridine add 11.0 g of pyruvoyl chloride and stir the resulting mixture at room temperature. Extract the reaction mixture with water and dry the organic layer over magnesium sulfate. Concentrate the dichloromethane solution in vacuo and distill the residue to give 1-pyruvoyl-cis,syn-octahydro-1H-indole-2(S)carboxylic acid, benzyl ester.

B. To 20 g of the product from part A in 400 ml of ethanol, add 2.0 g of 10% palladium-on-charcoal and hydrogenate at 50 psi at room temperature. Filter the resulting mixture and concentrate the filtrate in vacuo to give 1-pyruvoyl-cis,syn-octahydro-1H-indole-2(S)-carboxylic acid.

C. React 6.20 g of Nε-(benzyloxycarbonyl)-L-lysine ethyl ester in 20 ml of tetrahydrofuran with 4.8 g of 1-pyruvoyl-cis,syn-octahydro-1H-indole-2(S)-carboxylic acid and add 20 ml of molecular sieves 4A (Rohm and Haas). Stir the resulting mixute for 4 hours, add 12 g of sodium cyanoborohydride in 20 ml of methanol and stir the reaction mixture 20 hours. Filter, concentrate to dryness, and partition the residue between water and dichloromethane. Absorb the aqueous phase on strong acidic ion-exchange resin and elute with 4% pyridine in water to give 1-{N-[1(S)-ethoxycarbonyl-5-benzyloxycarbonylaminopentyl]-(R,S)-alanyl}-cis,syn-octahydro-1H-indole-2(S)-carboxylic acid. Separate the isomers on a column of silica gel using CHCl$_3$:isopropanol:7% ammonium hydroxide 1:1:1 (organic) as eluant to give 1-{N-[1(S)-ethoxycarbonyl-5-benzyloxycarbonylaminopentyl]-(S)-alanyl}-cis,syn-octahydro-1H-indole-2(S)-carboxylic acid.

D. Hydrogenate the product from C in 300 ml of ethanol using 1 g of 10% palladium-on-charcoal at 50 psi at room temperature. Filter the mixture and concentrate the filtrate to give 1-{N-[1(S)-ethoxycarbonyl-5-aminopentyl]-(S)-alanyl}-cis,syn-octahydro-1H-indole-2(S)-carboxylic acid.

EXAMPLE 6

1-{N-[1(S)-Ethoxycarbonyl-5-(4-chloro-3-sulfamoyl)-benzenesulfonaminopentyl]-(S)-alanyl}-cis,syn-octahydro-1H-indole-2(S)-carboxylic acid React 1.01 g of 1-{N-[1(S)-ethoxycarbonyl-5-aminopentyl]-(S)-alanyl}-cis,syn-octahydro-1H-indole-2(S)-carboxylic acid in 20 ml of tetrahydrofuran and 0.25 g of triethylamine with 0.75 g of 4-chloro-3-sulfamoylbenzenesulfonyl chloride and stir the resulting mixture at room temperature. Concentrate the resulting mixture in vacuo and chromatograph the residue on a Lobar RP-8 (E. Merck) size B column using acetonitrile:water as eluant to give the title compound.

EXAMPLE 7

1-{N-[1(S)-Ethoxycarbonyl-5-(4-chloro-3-sulfamoyl-benzamidopentyl]-(S)-alanyl}-cis,syn-octahydro-1H-indole-2(S)-carboxylic acid Treat 1.01 g. of 1-{N-[1(S)-ethoxycarbonyl-5-aminopentyl]-(S)-alanyl}-cis,syn-octahydro-1H-indole-2(S)-carboxylic acid in 20 ml of tetrahydrofuran and 0.25 g of triethylamine with 0.55 g of 4-chloro-3-sulfamoylbenzoyl chloride and stir the resulting mixture at room temperature. Concentrate the resulting mixture in vacuo and chromatograph the residue on a Lobar RP-8 (E. Merck) size B column using acetonitrile:water as eluant to give the title compound.

EXAMPLE 8

1-{N-[1(S)-Carboxy-5-aminopentyl]-(S)-alanyl}-cis,-syn-octahydro-1H-indole-2(S)-carboxylic acid To 4.04 g of 1-{N-[1(S)-ethoxycarbonyl-5-aminopentyl]-(S)-alanyl}-cis,syn-octahydro-1H-indole-2(S)-carboxylic acid in 100 ml of methanol:water 1:1 add 8 ml of 2.5 N NaOH at 0°–5° C. and then stir the resulting mixture at room temperature for 24 hours. Concentrate the resulting mixture and absorb on AG 50W-2 (Bio-Rad) resin (100–200 mesh, hydrogen form). Elute the resin with water, and then elute with 4% pyridine in water to yield the title compound.

EXAMPLE 9

1-{N-[1(S)-Carboxy-5-(4-chloro-3-sulfamoyl)benzamidopentyl]-(S)-alanyl}-cis,syn-octahydro-1H-indole-2(S)-carboxylic acid React 0.95 g of the product from Example 8 with 0.55 g of 4-chloro-3-sulfamoylbenzoyl chloride as described in Example 7 to give the title compound.

EXAMPLE 10

1-{N-[1(S)-Carboxy-5-(4-chloro-3-sulfamoyl)benzenesulfonamidopentyl]-(S)-alanyl}-cis,syn-octahydro-1H-indole-2(S)-carboxylic acid Treat 0.95 g of the product from Example 8 with 0.75 g of 4-chloro-3-sulfamoylbenzenesulfonyl chloride as described in Example 6 to give the title compound.

EXAMPLE 11

1-{N-[1(S)-Ethoxycarbonyl-5-aminopentyl]-(R,S)-alanyl}-(S)-proline

Make a solution of Nε-benzyloxycarbonyl-L-lysine ethyl ester hydrochloride (2.94 g) in water (10 ml) basic with 15 ml of saturated aqueous potassium bicarbonate and extract with CH$_2$Cl$_2$. Dry the extract over MgSO$_4$ and concentrate to dryness. Dissolve the residue, Nε-Benzyloxycarbonyl-L-lysine ethyl ester, in tetrahydrofuran (20 ml) and pyruvoylproline (555 mg) and add powdered No. 4A molecular sieves (1.0 g). Stir the mixture at room temperature for 4 hours. Add sodium cyanoborohydride (630 mg) in 1 ml of methanol over 2 hours and stir the mixture overnight. Filter the mixture, concentrate to dryness, and partition the residue between water (10 ml) and CH$_2$Cl$_2$ (15 ml). Absorb the aqueous phase on strong acid ion-exchange resin and elute with 4% pyridine in water to yield 470 mg of 1-{N-(1(S)-ethoxycarbonyl-5-benzyloxycarbonylaminopentyl]-R,S-alanyl}-S-proline. Remove the protecting group by hydrogenation in ethanol:water 1:1 over 10% Pd/C catalyst at 40 psi. Filter the mixture and take the filtrate to dryness. Chromatograph the residue in methanol on an LH-20 column to give the desired 1-{N-[1(S)-ethoxy-carbonyl-5-aminopentyl]-(R,S)-alanyl}-(S)-proline.

EXAMPLE 12

1-{N-[1(S)-Ethoxycarbonyl-5-(4-chloro-3-sulfamoyl)-benzenesulfonamidopentyl]-(R,S)-alanyl}-(S)-proline Condense 0.90 g of 1-{N-[1(S)-ethoxycarbonyl-5-aminopentyl]-(R,S)-alanyl}-(S)-proline with 0.75 g of 4-chloro-3-sulfamoylbenzenesulfonyl chloride as described in Example 6 to give the title compound.

EXAMPLE 13

1-{N-[1(S)-Ethoxycarbonyl-5-(4-chloro-3-sulfamoyl)-benzamidopentyl]-(R,S)-alanyl}-(S)-proline React 0.90 g of 1-{N-[1(S)-ethoxycarbonyl-5-aminopentyl]-(R,S)-alanyl}-(S)-proline with 0.55 g of 4-chloro-3-sulfamoylbenzoylchloride as described in Example 7 to give the title compound.

EXAMPLE 14

1-{N-[1(S)-Carboxy-5-aminopentyl]-(R,S)-alanyl}-(S)-proline

Treat 3.50 g of 1-{N-[1(S)-ethoxycarbonyl-5-aminopentyl]-(R,S)-alanyl}-(S)-proline in 100 ml of methanol:water 1:1 with 810 ml of 2.5 N NaOH as described in Example 8 to give the title compound.

EXAMPLE 15

1-{N-1(S)-Carboxy-5-(4-chloro-3-sulfamoyl)benzenesulfonamidopentyl]-(R,S)-alanyl}-(S)-proline Condense 0.80 g of 1-{N-[1(S)-carboxy-5-aminopentyl]-(R,S)-alanyl}-(S)-proline with 0.75 g of 4-chloro-3sulfamoylbenzenesulfonyl chloride as described in Example 6 to give the title compound.

EXAMPLE 16

1-{N-[1(S)-Carboxy-5-(4-chloro-3-sulfamoyl)benzamidopentyl]-(R,S)-alanyl}-(S)-proline React 0.80 g 1- N-[1(S)-carboxy-5-aminopentyl]-(R,S)-alanyl-(S)-proline with 0.55 g of 4-chloro-3-sulfamoylbenzoyl chloride as described in Example 7 to give the title compound.

The compounds of this invention are useful as antihypertensive agents in mammals, including humans, in which the blood pressure has become abnormally elevated. It is believed that the compounds of the present invention act to alleviate or reduce hypertension because they act both as angiotensin converting enzyme inhibitors and as diuretics.

The compounds of the present invention can be combined with pharmaceutical carriers and administered in a variety of well known pharmaceutical forms suitable for oral or parenteral administration to provide compositions useful in the treatment of cardiovascular disorders and particularly mammalian hypertension.

The effective dose (ED$_{50}$) of the compounds of this invention will typically be in the range of about 0.1 to about 10 mg/kg, of mammalian weight, administered in single or divided doses. The exact dose to be administered is dependent upon where the particular compound lies within the above quoted range, as well as upon the age, weight and condition of the individual.

Generally, in treating humans, the compounds of this invention may be administered to patients in need of such treatment in a dosage range of 5 to 500 mg per patient generally given several times, thus giving a total daily dose of from 5 to 2000 mg per day.

The composition containing the compounds of this invention will preferably contain from about 5 to about 250 mg of the active compound per dosage unit. These compositions are most preferably administered orally. Typical formulations for oral administration are those such as tablets, capsules, syrups, elixirs or suspensions. Typical injectable formulations include solutions and suspensions.

The typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose; ethyl cellulose and methyl cellulose; calcium phosphates such as dicalcium phosphate and tri-calcium phosphate; sodium sulfate; calcium sulfate; polyvinylpyrrolidone, polyvinyl alcohol; stearic acid; alkaline earth metal stearates such as magnesium stearate and calcium stearate, stearic acid vegetable oils such as peanut oil, cottonseed oil, sesame oil, olive oil and corn oil; non-ionic, cationic and anionic surfactants; ethylene gylcol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

The following examples describe in detail compositions that are illustrative of the present invention. It will be apparent to those skilled in the art that many modifications, both of materials and methods, may be practiced without departing from the purpose and intent of this disclosure.

In the following examples, the "active ingredient" is 1-{N-[1(R)-Carboxy-2-[S-((3-(6-chloro-3,4-dihydro-7-sulfamoyl-1,2,4-benzothiadiazinyl-1,1-dioxide)methyl))thio]ethyl]]-(S)-alanyl}-cis,syn-octahydro-1$\underline{H}$-indole-2(S)-carboxylic acid.

EXAMPLE 17

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.0 | 250.0 |

Blend the active ingredient, lactose and corn starch until uniform; then blend the magnesium stearate into the resulting powder. Encapsulate the mixture into suitably sized two-piece hard gelatin capsules.

EXAMPLE 18

| Tablet | Amount (mg) | |
|---|---|---|
| Active ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ⅜ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 19

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–35° C. Charge and dissolve all other excipients and the active ingredient. Bring the solution to final volume, filter it through a sterilizing membrane and fill into sterile containers.

Similarly, substitute other compounds of the present invention (for example, the title compound of Example 6 or the title compound of Example 7) to prepare other compositions of the present invention.

We claim:

1. A compound of the formula

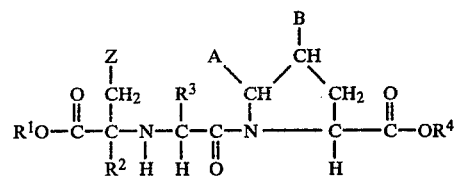

or a pharmaceutically acceptable salt thereof, wherein $R^1$, $R^2$ and $R^4$ are independently selected from hydrogen and lower alkyl; $R^3$ is hydrogen, lower alkyl or amino lower alkyl; A and B taken together with the carbons to which they are attached form an alkylene ring having six carbon atoms or A and B are hydrogen; and Z is

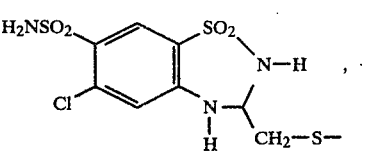

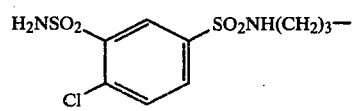

or

-continued

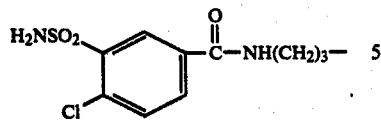 5

2. A compound according to claim 1 wherein $R^2$ is hydrogen.

3. A compound according to claim 1 wherein $R^4$ is hydrogen.

4. A compound according to claim 1 wherein A and B taken together with the carbons to which they are attached form an alkylene ring having six carbon atoms.

5. A compound according to claim 4 wherein $R^2$ is hydrogen.

6. A compound according to claim 4 wherein $R^4$ is hydrogen.

7. A compound according to claim 6 wherein $R^2$ is hydrogen.

8. A compound according to claim 1 or 7 wherein $R^3$ is

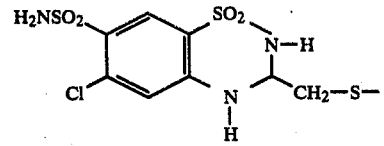

9. A compound according to claim 1 or 7 wherein $R^3$ is

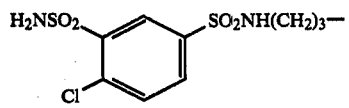

10. A compound according to claim 1 or 7 wherein $R^3$ is

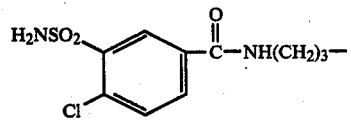

11. A method of treating hypertension in mammals comprising administering to a mammal in need of such treatment an effective amount of a compound according to claim 1.

12. A pharmaceutical composition comprising an antihypertensive effective amount of a compound according to claim 1.

* * * * *